United States Patent [19]

Pedersen et al.

[11] Patent Number: 4,613,711

[45] Date of Patent: Sep. 23, 1986

[54] INDENES BY CATALYTIC DEHYDROCYCLIZATION

[75] Inventors: S. Erik Pedersen, Solon; Wilfrid G. Shaw, Lyndhurst; Linda L. Pfingsten, Columbia, all of Ohio

[73] Assignee: The Standard Oil Company, Cleveland, Ohio

[21] Appl. No.: 801,355

[22] Filed: Nov. 25, 1985

[51] Int. Cl.[4] .............................................. C07C 12/64
[52] U.S. Cl. ................................. 585/411; 585/407; 585/420; 585/442; 585/444
[58] Field of Search ............... 585/406, 407, 411, 418, 585/420, 442, 444

[56] References Cited

U.S. PATENT DOCUMENTS

| | | | |
|---|---|---|---|
| 2,531,328 | 11/1950 | Elwell | 585/411 |
| 2,823,240 | 2/1958 | Field et al. | 585/411 |
| 2,916,529 | 12/1959 | Sanford et al. | 585/411 |
| 3,223,742 | 12/1965 | Eberhardt | 585/411 |
| 4,255,601 | 3/1981 | Kuch et al. | 585/411 |
| 4,292,456 | 9/1981 | Kiikka | 585/410 |
| 4,374,293 | 2/1983 | Burrington et al. | 585/410 |

*Primary Examiner*—Curtis R. Davis
*Attorney, Agent, or Firm*—Charles S. Lynch; John E. Miller; Larry W. Evans

[57] ABSTRACT

Disclosed is the dehydrocyclization of certain alkylaromatics to indene or a substituted indene by contacting certain alkylaromatics in admixture with $H_2O$ with a sulfided metal oxide catalyst.

6 Claims, No Drawings

INDENES BY CATALYTIC DEHYDROCYCLIZATION

This invention relates to a method of dehydrocyclizing certain alkylaromatics to indene or substituted indenes.

Indenes are currently prepared industrially by isolation from coal tar or petroleum distillates. This method yields indene of too low a purity to be useful for preparation of high HDT polymers without extensive and costly purification. High purity indene is not currently an item of commerce in more than research quantities. Syntheses of indene have traditionally relied upon cumbersome, multi-step non-catalytic methods which are not industrially useful because of their inherently low yields and poor product recovery as well as their requirement of highly acidic reaction conditions (see, for example, Wittig. G. *Chem. Ber.* 91, 1958, 895 or Waldman and Schwenk, *Ann.* 487, 1931, 287; or Ulman and Lehner, *Ber.* 38, 1905, 729; or Weedon and Wahler, *J. Am. Chem. Soc.* 33, 1905, 386.

It is an object of the present invention to provide a process for making indenes synthetically.

It is a further object to provide a new method for making indenes by the vapor phase catalytic dehydrogenation of certain alkylaromatics.

It is a more specific object to provide a method for the catalytic dehydrocyclization of o-ethyltoluene to indene at good conversions and yields.

Other objects, as well as aspects, features, and advantages, of the invention will be apparent from the disclosure and claims.

These and other objects are realized by the present invention according to which there is provided a process which comprises the vapor phase dehydrocyclization of an alkylaromatic of the formula:

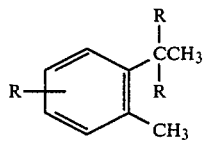

in the presence of $H_2S$ and a solid catalyst to make an indene of the formula

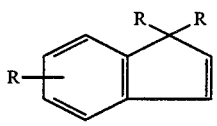

wherein each R is independently selected from H, a $C_1$ to $C_4$ alkyl group, and phenyl wherein said catalyst is the product of sulfiding a solid catalyst precursor having 2-40 weight percent of at least one oxide selected from CoO, NiO, $MoO_3$ and $WO_3$ (any 1, 2, 3 or 4 of these make up the 2-40 percent) on 60-98 weight percent of an alumina support, said sulfiding comprising treating said catalyst precursor at an elevated temperature with a mixture of gases containing hydrogen sulfide and hydrogen, said catalyst having a surface area (BET method) less than 100 $m^2/gm$., usually 1 to 80 $m^2/gm$.

We are not aware of any similar art relative to the production of indenes. The closest art known to use is the cyclization of certain alkylaromatics catalyzed by acids and by metals (Ado. Cat. 28, 293, 1979). Reactions of this type are generally not very selective and give only poor conversion to indenes.

The catalyst precursor in an especially useful embodiment of our invention can have 1-10 weght percent CoO and 5-40 weight percent $MoO_3$ and 60-80 weight percent alumina, wherein the weight ratio of Co to Mo s in the range 1/2.5 to 1/6.

The high temperature of the treatment of the catalyst precursor with $H_2S$ and reducing agent $H_2$ is ordinarily in the range 200°–750° C., usually 325°–500° C. Time of treatment in such temperature range is from 10 minutes to 5 hours in most instances, longer times being used at lower temperature ranges, and the treatment can be at a range of temperatures as in the examples herein. The mole ratio of $H_2$ to $H_2S$ can vary widely, from 1:10 to 10:1, and even outside these limits, but is usually in the range 1:4 to 2:1. In practice, the sulfiding reaction is controlled by beginning the treatment at temperatures as low as ambient temperatures and only gradually raising the temperatures, in order to prevent a runaway exothermic temperature rise. Of course, in a less practical manner the exotherm could be controlled by limiting the rate at which $H_2$ and $H_2S$ is made available to contact the catalyst precursor oxides.

In the reaction of the invention the ratio of $H_2S$ to the alkylaromatic feed is generally in the range of 1–50 moles $H_2S$ per mole of alkylaromatic; but usually preferred is the range 5–15 moles $H_2S$ per mole of alkylaromatic. Contact time can be controlled by diluting the reactants wth an inert gas such as ntrogen.

When the hydrocarbon is o-ethyltoluene, the major by-product in the reaction is 2-methylstyrene. This product has been shown to be an intermediate in the formation of indene and may be recycled. Thus, the feed to the reactlon can contain 2-methylstyrene, as well as o-ethyltoluene.

If a catalyst is employed having a much higher surface area than here specified, a great deal of cracking or decomposition occurs. If the oxide precursor has had its surface area reduced, but without the $H_2S$ treatment, little reaction takes place, but when the latter catalyst is sulfided as set forth herein, conversion to indene increases significantly.

The function of $H_2S$ in the dehydrocyclization of the alkylaromatic to an indene is not well understood. However, one effect that its use appears to have is to suppress coke or carbon formation, thus allowing for a longer operating time.

The following examples are merely illustrative and are not to be considered in any way limiting.

EXAMPLE 1

A catalyst was made from a catalyst precursor which consisted of 3.5 weight percent CoO and 12.5 weight percent $MoO_3$ on an alumina support (84 percent) in the form of 1/16 inch spherical pellets. The precursor had a surface area (BET method) of 236 sq. meters/gram. It was reduced in surface area to 1.65 $m^2/gm$. by heating for 2 hours at 1100° C. It was then sulfided by placing 20 cc in a 3/8 inch stainless steel tube (about 12.5 grams). 260 cc per minute of a gas mixture (25° C.) was passed over the catalyst in the tube at the rate of 260 cc/min. The composition in mole percent of this sulfiding stream was 13.35 percent $H_2S$, 5.88 percent $H_2$, and 80.77 percent $N_2$. This gas mixture was passed over the catalyst for 2 hours, starting with catalyst tube temperature of about 25° C. and raising the temperature at an essentially uniform rate to a temperature of 450° C. at the end of the two hour period.

EXAMPLE 2

20 cc of the catalyst of Example 1 were placed in a stainless steel tubular reactor having an I.D. of about 3/8 inch. The ortho ethyltoluene was introduced to the tubular reactor by bubbling $N_2$ gas through it and into the reactor, and $H_2S$ was introduced as a separate stream. The molar ratio of the gases fed was $12H_2S:15.7N_2:1$ o-ethyltoluene, the reactor temperature was 600° C. and the contact time was 1.3 seconds. Under these conditions conversion of the feed hydrocarbon was 48.8 percent, the yield of indene was 10.8 percent and the yield of 2-methylstyrene was 32.6 percent.

EXAMPLE 3

A catalyst was made from a catalyst precursor which consisted of 3.5 weight percent CoO and 12.5 weight percent $MoO_3$ on an alumina support (84 percent) in the form of 1/16 inch spherical pellets. The precursor had a surface area (BET method) of 236 sq. meters/gram. It was reduced in surface area to 53.0 m$^2$/gm. by heating for 2 hours at 900° C. It was then sulfided by placing 20 cc in a 3/8 inch stainless steel tube (about 12.5 grams). 260 cc per minute of a gas mixture (25° C.) was passed over the catalyst in the tube at the rate of 260 cc/min. The composition in mole percent of this sulfiding stream was 13.35 percent $H_2S$, 5.88 percent $H_2$, and 80.77 percent $N_2$. This gas mixture was passed over the catalyst for 2 hours, starting with catalyst tube temperature of about 25° C. and raising the temperature at an essentially uniform rate to a temperature of 450° C. at the end of the two-hour period.

EXAMPLE 4

20 cc of the catalyst of Example 3 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $12H_2S:17.3N_2:1$ o-ethyltoluene, the reactor temperature was 600° C. and the contact time was 1.4 seconds. Under these conditions conversion of the feed hydrocarbon was 57.2 percent, the yield of indene was 24 percent and the yield of 2-methylstyrene was 29 percent.

EXAMPLE 5

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $8H_2S:15.7N_2:1$ o-ethyltoluene, the reactor temperature was 600° C. and the contact time was 2.3 seconds. Under these conditions conversion of the feed hydrocarbon was 45.9 percent, the yield of indene was 11.6 percent and the yield of 2-methylstyrene was 30.7 percent.

EXAMPLE 6

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $4.H_2S:15.7N_2:1$ o-ethyltoluene, the reactor temperature was 600° C. and the contact time was 2.6 seconds. Under these conditions conversion of the feed hydrocarbon was 38.7 percent, the yield of indene was 6.8 percent and the yield of 2-methylstyrene was 29.9 percent.

EXAMPLE 7

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $12H_2S:15.7N_2:1$ o-ethyltoluene, the reactor temperature was 550° C. and the contact time was 1.4 seconds. Under these conditions conversion of the feed hydrocarbon was 26.8 percent, the yield of indene was 2.3 percent and the yield of 2-methylstyrene was 23.4 percent.

EXAMPLE 8

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $4.1H_2S:15.7N_2:1$ o-ethyltoluene, the reactor temperature was 650° C. and the contact time was 1.7 seconds. Under these conditions conversion of the feed hydrocarbon was 58.3 percent, the yield of indene was 19.3 percent and the yield of 2-methylstyrene was 31.8 percent.

EXAMPLE 9

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $8H_2S:15.7N_2:1$ o-ethyltoluene, the reactor temperature was 650° C. and the contact time was 1.4 seconds. Under these conditions conversion of the feed hydrocarbon was 59.3 percent, the yield of indene was 22.9 percent and the yield of 2-methylstyrene was 27.9 percent.

EXAMPLE 10

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $12H_2S:15.7N_2:1$ o-ethyltoluene, the reactor temperature was 650° and the contact time was 1.2 seconds. Under these conditions conversion of the feed hydrocarbon was 59.8 percent, the yield of indene was 26.3 percent and the yield of 2-methylstyrene was 26.6 percent.

EXAMPLE 11

A catalyst was made from a catalyst precursor which consisted of 3.5 weight percent CoO and 12.5 weight percent $MoO_3$ on an alumina support (84 percent) in the form of 1/16 inch spherical pellets. The precursor had a surface area (BET method) of 236 sq. meters/gram. It was reduced in surface area to 2.63 m$^2$/gm. by heating for 2 hours at 932° C. It was then sulfided by placing 20 cc in a ⅜ inch stainless steel tube (about 12.5 grams). 260 cc per minute of a gas mixture (25° C.) was passed over the catalyst in the tube at the rate of 260 cc/min. The composition in mole percent of this sulfiding stream was 13.35 percent H$_2$S, 5.88 percent H$_2$, and 80.77 percent N$_2$. This gas mixture was passed over the catalyst for 2 hours, starting with catalyst tube temperature of about 25° C. and raising the temperature of an essentially uniform rate to a temperature of 450° C. at the end of the two-hour period.

EXAMPLE 12

20 cc of the catalyst of Example 11 were placed in a stainless steel tubular reactor having an I.D. of about ⅜ inch. The ortho ethyltoluene was introduced to the tubular reactor by bubbling N$_2$ gas through it and into the reactor, and the H$_2$S was introduced as a separate stream. The molar ratio of the gases fed was 12H$_2$S:17.3N$_2$:1 o-ethyltoluene, the reactor temperature was 650° C. and the contact time was 1.3 seconds. Under these conditions conversion of the feed hydrocarbon was 66.1 percent, the yield of indene was 31.2 percent and the yield of 2-methylstyrene was 28.1 percent.

EXAMPLE 13

A catalyst was made from a catalyst precursor which consisted of 3.5 weight percent CoO and 12.5 weight percent MoO$_3$ on an alumina support (84 percent) in the form of 1/16 inch spherical pellets. The precursor had a surface area (BET method) of 236 sq. meters/gram. It was reduced in surface area to 13.3 m$^2$/gm. by heating for 2 hours at 913° C. It was then sulfided by placing 20 cc in a ⅜ inch stainless steel tube (about 12.5 grams). 260 cc per minute of a gas mixture (25° C.) was passed over the catalyst in the tube at the rate of 260 cc/min. The composition in mole percent of this sulfiding stream was 13.35 percent H$_2$S, 5.88 percent H$_2$, and 80.77 percent N$_2$. This gas mixture was passed over the catalyst for 2 hours, starting with catalyst tube temperature of about 25° C. and raising the temperature of an essentially uniform rate to a temperature of 450° C. at the end of the two-hour period.

EXAMPLE 14

20 cc of the catalyst of Example 13 were placed in a stainless steel tubular reactor having an I.D. of about ⅜ inch. The ortho ethyltoluene was introduced to the tubular reactor by bubbling N$_2$ gas through it and into the reactor, and the H$_2$S was introduced as a separate stream. The molar ratio of the gases fed was 12H$_2$S:17.3N$_2$:1 o-ethyltoluene, the reactor temperature was 650° C. and the contact time was 1.3 seconds. Under these conditions conversion of the feed hydrocarbon was 74.7 percent, the yield of indene was 36.8 percent and the yield of 2-methylstyrene was 30.9 percent.

EXAMPLE 15

20 cc of the catalyst of Example 3 were placed in a stainless steel tubular reactor having an I.D. of about ⅜ inch. The ortho ethyltoluene was introduced to the tubular reactor by bubbling N$_2$ gas through it and into the reactor, and the H$_2$S was introduced as a separate stream. The molar ratio of the gases fed was 12H$_2$S:17.3N$_2$:1 o-ethyltoluene, the reactor temperature was 650° C. and the contact time was 1.3 seconds. Under these conditions conversion of the feed hydrocarbon was 55.9 percent, the yield of indene was 35.7 percent and the yield of 2-methylstyrene was 13.1 percent.

EXAMPLE 16

Into a ⅜ inch I.D. stainless steel tubular reactor containing 20 cc of the catalyst of Example 3 was introduced ortho ethyltoluene in a stream of nitrogen gas, together with a separate stream of hydrogen sulfide, in the molar ratios 12H$_2$S:17.3N$_2$:1 o-ethyltoluene. The reactor temperature was 700° C. and the contact time was 1.2 seconds. Conversion of the o-ethyltoluene was 64.2 percent, the yield of indene was 40.5 percent and the yield of 2-methylstyrene was 9.3 percent.

EXAMPLE 17

20 cc of the catalyst of Example 13 were placed in a stainless steel tubular reactor having an I.D. of about ⅜ inch. The ortho ethyltoluene was introduced to the tubular reactor by bubbling N$_2$ gas through it and into the reactor, and the H$_2$S was introduced as a separate stream. The molar ratio of the gases fed was 12H$_2$S:17.3N$_2$:1 o-ethyltoluene, the reactor temperature was 700° C. and the contact time was 1.2 seconds. Under these conditions conversion of the feed hydrocarbon was 80.3 percent, the yield of indene was 51.2 percent and the yield of 2-methylstyrene was 12.3 percent.

EXAMPLE 18

Into a ⅜ inch I.D. stainless steel tubular reactor containing 20 cc of the catalyst of Example 11 was introduced ortho ethyltoluene in a stream of nitrogen gas, together with a separate stream of hydrogen sulfide. in the molar ratios 12H$_2$S:17.3N$_2$:1 o-ethyltoluene. The reactor temperature was 700° C. and the contact time was 1.2 seconds. Conversion of the o-ethyltoluene was 85.0 percent, the yield of indene was 55.0 percent and the yield of 2-methylstyrene was 12.6 percent.

EXAMPLE 19

20 cc of the catalyst of Example 1 were placed in a stainless steel tubular reactor having an I.D. of about ⅜ inch. The ortho ethyltoluene was introduced to the tubular reactor by bubbling N$_2$ gas through it and into the reactor, and the H$_2$S was introduced as a separate stream. The molar ratio of the gases fed was 12H$_2$S:17.3N$_2$:1 o-ethyltoluene, the reactor temperature was 700° C. and the contact time was 1.2 seconds. Under these conditions conversion of the feed hydrocarbon was 74.3 percent, the yield of indene was 46.1 percent and the yield of 2-methylstyrene was 12 percent.

EXAMPLE 20

Into a ⅜ inch I.D. stainless steel tubular reactor containing 20 cc of the catalyst of Example 1 was introduced ortho ethyltoluene in a stream of nitrogen gas, together with a separate stream of hydrogen-sulfide, in the molar ratios 14H$_2$S:15.7N$_2$:1 o-ethyltoluene. The reactor temperature was 700° C. and the contact time was 1.1 seconds. Conversion of the o-ethyltoluene was 74.0 percent, the yield of indene was 49.4 percent and the yield of 2-methylstyrene was 10.4 percent.

EXAMPLE 21

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $16H_2S:15.7N_2:1$ o-ethyltoluene, the reactor temperature was 700° C. and the contact time was 1.0 seconds. Under these conditions conversion of the feed hydrocarbon was 71.1 percent, the yield of indene was 46.8 percent and the yield of 2-methylstyrene was 10.8 percent.

EXAMPLE 22

Into a ⅜ inch I.D. stainless steel tubular reactor containing 20 cc of the catalyst of Example 1 was introduced ortho ethyltoluene in a stream of nitrogen gas, together with a separate stream of hydrogen sulfide, in the molar ratios $31.7H_2S:15.7N_2:1$ o-ethyltoluene. The reactor temperature was 700° C. and the contact time was 0.72 seconds. Conversion of the o-ethyltoluene was 67.8 percent, the yield of indene was 43.8 percent and the yield of 2-methylstyrene was 13.4 percent.

EXAMPLE 23

20 cc of the catalyst of Example 11 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $12H_2S:17.3N_2:1$ o-ethyltoluene, the reactor temperature was 710° C. and the contact time was 1.2 seconds. Under these conditions conversion of the feed hydrocarbon was 86.4 percent, the yield of indene was 58.0 percent and the yield of 2-methylstyrene was 8.8 percent.

EXAMPLE 24

20 cc of the catalyst of Example 1 were placed in a stainless steel tubular reactor having an I.D. of about ⅜ inch. The ortho ethyltoluene was introduced to the tubular reactor by bubbling $N_2$ gas through it and into the reactor, and the $H_2S$ was introduced as a separate stream. The molar ratio of the gases fed was $16H_2S:15.7N_2:1$ o-ethyltoluene, the reactor temperature was 740° C. and the contact time was 1.0 seconds. Under these conditions conversion of the feed hydrocarbon was 61.1 percent, the yield of indene was 40.2 percent and the yield of 2-methylstyrene was 0.9 percent.

EXAMPLE 25

Into a ⅜ inch I.D. stainless steel tubular reactor containing 20 cc of the catalyst of Example 1 was introduced ortho ethyltoluene and 2-methylstyrene, each entrained in nitrogen gas, together with a separate stream of hydrogen sulfide. The molar ratio of o-ethyltoluene to 2-methylstyrene was 2:1. The molar ratios of $H_2S$ to $N_2$ to hydrocarbon substrate (o-ethyltoluene plus 2-methylstyrene) was $12H_2S:16.9N_2:1$ hydrocarbon. The reactor temperature was 700° C. and the contact time was 1.05 seconds. Conversion of the o-ethyltoluene was 87.4 percent, the yield of indene was 59.3 percent, based on the combined hydrocarbon fed to the reactor, and the "yield" of 2-methylstyrene was 14.3 percent on the same basis.

EXAMPLE 26

Into a ⅜ inch I.D. stainless steel tubular reactor containing 20 cc of the catalyst of Example 1 was introduced ortho ethyltoluene and 2-methylstyrene, each entrained in nitrogen gas, together with a separate stream of hydrogen sulfide. The molar ratio of o-ethyltoluene to 2-methylstyrene was 2:1. The molar ratios of $H_2S$ to $N_2$ to hydrocarbon substrate (o-ethyltoluene plus 2-methylstyrene) was $12H_2S:16.9N_2:1$ hydrocarbon. The reactor temperature was 695° C. and the contact time was 0.98 seconds. Conversion of the o-ethyltoluene was 79.5 percent, the yield of indene was 54.9 percent, based on the combined hydrocarbon fed to the reactor, and the "yield" of 2-methylstyrene was 13.6 percent on the same basis.

As will be evident to those skilled in the art various modifications of this invention can be made or followed in the light of the foregoing disclosure and discussion without departing from the spirit and scope of the disclosure or from the scope of the claims.

We claim:

1. A process which comprises the vapor phase dehydrocyclization of an alkylaromatic of the formula:

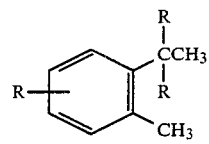

in the presence of $H_2S$ and a solid catalyst to make an indene of the formula

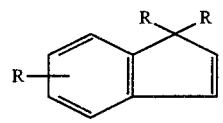

wherein each R is independently selected from H, a $C_1$ to $C_4$ alkyl group, and phenyl wherein said catalyst is the products of sulfiding a solid catalyst precursor having 2-40 weight percent of at least one oxide selected from CoO, NiO, $MoO_3$ and $WO_3$ on 60-98 weight percent of an alumina support, said sulfiding comprising treating said catalyst precursor at an elevated temperature with a mixture of gases containing hydrogen sulfide and hydrogen, said catalyst having a surface area (BET method) less than 100 $m^2/gm$.

2. A process according to claim 1 wherein said surface area is 1-80 $m^2/gm$.

3. A process according to claim 1 wherein the gases initially contacting the catalyst contain $H_2S$ and o-ethyltoluene in a ratio in the range of 1-50 moles of $H_2S$ per mole of o-ethyltoluene.

4. A process according to claim 1 wherein the gases initially contacting the catalyst contain $H_2S$ and o-ethyltoluene in a ratio in the range of 5-15 moles of $H_2S$ per mole of o-ethyltoluene.

5. A process of claim 1 wherein the gases initially contacting the catalyst contains 2-methylstyrene in addition to $H_2S$ and o-ethyltoluene.

6. A process of claim 2 wherein the gases initially contacting the catalyst contains 2-methylstyrene in addition to $H_2S$ and o-ethyltoluene.

* * * * *